United States Patent [19]

Lobregt et al.

[11] Patent Number: 6,097,833
[45] Date of Patent: Aug. 1, 2000

[54] IMAGE COMPOSITION METHOD AND IMAGING APPARATUS FOR PERFORMING SAID METHOD

[75] Inventors: Steven Lobregt; Alexander H. W. Van Eeuwijk, both of Eindhoven, Netherlands

[73] Assignee: U.S. Philips Corporation, New York, N.Y.

[21] Appl. No.: 08/926,867

[22] Filed: Sep. 10, 1997

Related U.S. Application Data

[63] Continuation of application No. 08/345,029, Nov. 23, 1994, abandoned.

[30] Foreign Application Priority Data

Nov. 26, 1993 [EP] European Pat. Off. .............. 93203320

[51] Int. Cl.[7] ....................................................... G06K 9/00
[52] U.S. Cl. ...................... 382/130; 378/98.12; 382/384
[58] Field of Search ..................................... 382/282, 294, 382/300, 130, 131, 132, 278, 284, 307; 342/179; 345/426; 348/451, 452, 458, 459, 580, 581, 584, 585, 586, 595, 597, 598; 378/62, 98, 98.11, 98.12, 146, 160

[56] References Cited

U.S. PATENT DOCUMENTS

| | | | |
|---|---|---|---|
| 4,504,923 | 3/1985 | Schlunt et al. ........................... | 364/728 |
| 4,613,983 | 9/1986 | Yedid et al. ........................... | 378/98.12 |
| 4,644,575 | 2/1987 | Kruger et al. ........................... | 378/98.4 |
| 4,797,942 | 1/1989 | Burt ........................................ | 382/284 |
| 4,870,692 | 9/1989 | Zuiderveld et al. ..................... | 382/107 |
| 5,063,375 | 11/1991 | Lien et al. .............................. | 340/703 |
| 5,117,446 | 5/1992 | Haaker et al. .......................... | 378/98.3 |
| 5,123,056 | 6/1992 | Wilson .................................... | 382/132 |
| 5,178,146 | 1/1993 | Giese ..................................... | 128/653.2 |
| 5,231,675 | 7/1993 | Sarr et al. ............................... | 382/152 |
| 5,347,570 | 9/1994 | Haaks .................................... | 378/98.12 |
| 5,384,573 | 1/1995 | Turpin .................................... | 342/179 |
| 5,394,520 | 2/1995 | Hall ........................................ | 395/135 |
| 5,488,674 | 1/1996 | Burt et al. .............................. | 382/284 |
| 5,657,402 | 8/1997 | Bender et al. .......................... | 382/284 |
| 5,892,554 | 4/1999 | DiCicco et al. ........................ | 382/284 |

FOREIGN PATENT DOCUMENTS 0576066  12/1993  European Pat. Off. .

OTHER PUBLICATIONS

J.C. Curlander and R.N. McDonough, Synthetic ApertureRadar Systems and Signal Processing, John Wiley and Sons, Chapter 8.4.1, p. 412, Jan. 1991.

*Primary Examiner*—Jon Chang
*Assistant Examiner*—Jayanti K. Patel
*Attorney, Agent, or Firm*—Dwight H. Renfrew

[57] ABSTRACT

Sub-images are merged in order to form an assembled image representing an elongate scene. In order to counteract artifacts in the assembled image such as disturbing transitions at the boundaries of adjacent sub-images in the image assembly method in accordance with the invention, pixel-values of overlapping portions of consecutive sub-images are interpolated so as to form pixel-values of the assembled image. The relative shift between consecutive sub-images with respect to the elongate scene is calculated from image information contained in the sub-images themselves. Correlations of pixel-values in overlapping portions of consecutive sub-images are determined as a function of the shift-value of the shift between consecutive sub-images with respect to the elongate scene. The actual shift between consecutive sub-images is found as the shift-value for which the correlation attains its maximum-value. The image assembly method in accordance with the invention is particularly suitable for use in peripheral x-ray angiography. Consecutive sub-images are made by x-irradiations of e.g. a patient's leg with an x-ray imaging system comprising an x-ray source, an x-ray detector, in various positions relative to the patient. In order to induce a sufficient amount of contrast in the sub-images to enable the determination of the relative shift between consecutive sub-images the invention proposes to image a contrasting object together with the elongate scene itself. Preferably the contrasting object has the form of a ruler with a binary pattern which may be incorporated in the patient table.

26 Claims, 6 Drawing Sheets

IMAGE COMPOSITION METHOD AND IMAGING APPARATUS FOR PERFORMING SAID METHOD

This is a continuation of application Ser. No. 08/345,029, filed Nov. 23, 1994, now abandoned.

BACKGROUND OF THE INVENTION

1. Field of the Invention

The invention relates to an image composition method comprising the steps of making a series of consecutive sub-images each representing a portion of an elongate scene, which sub-images overlap along the elongate scene, and of merging the sub-images into an assembled image. The invention also relates to an image processor for performing said method. The invention further relates to an x-ray examination apparatus comprising an image processor for performing said method.

2. Description of the Related Art

An image composition method of said kind and a device for performing this method are known from the United States Patent U.S. Pat. No. 5,123,056.

The cited reference describes, in particular, an image composition method for use in peripheral angiography by means of x-ray radiography. The x-ray examination apparatus described in the cited reference comprises an x-ray source, an x-ray detector facing the x-ray source and a patient table. The patient table on the one hand, and the x-ray source and the x-ray detector on the other hand, are displaceable with respect to one another. Consecutive sub-images of adjacent portions of a patient's limb are made by successive irradiations while the patient is translated vis-à-vis the x-ray source over some distance between successive irradiations. X-ray imaging is performed on the patient's limb in peripheral angiography. Because of the size of the limb of interest, an x-ray examination apparatus is unable to image the entire limb at once during a single irradiation step. Instead, a number of x-ray sub-images are made of a patient's limb that is to be examined. These x-ray sub-images are converted into electronic sub-images by means of an x-ray image detector in the form of an image intensifier television chain that is included in the x-ray examination apparatus. In order to form a single image of the entire limb, the electronic sub-images are processed in such a way that overlapping portions of said electronic sub-images are deleted. Subsequently, from said processed electronic sub-images, an assembled image is formed by adjoining consecutive processed electronic sub-images. The assembled image is supplied in the form of an electronic videosignal which may be supplied to a monitor for direct viewing or to a device for forming a hard-copy of the assembled image.

In the image composition method of the cited reference the overlapping portions of consecutive sub-images are calculated from positions of a carrier to which the x-ray source and the x-ray detector are mounted, and from positions of the patient table of the x-ray apparatus during x-irradiation for the formation of each of the x-ray sub-images. Thus, the known image assembly method can be employed only if data on the positions of the x-ray source, x-ray detector and patient table are recorded together with the x-ray sub-images. It is common practice to fit an x-ray examination apparatus with a device for measuring and recording such positions. Consequently the known method suffers from a substantial drawback in that the known method is unsuitable for forming an assembled image from sub-images produced by an x-ray examination apparatus which does not record positions of the carrier and the patient table. In each of the sub-images, moreover, image-distortions arise, such as pincushion-distortion caused by the curvature of the entrance screen of the image intensifier, S-distortion caused by stray magnetic fields which perturb the electron-optics of the image intensifier, vignetting caused by to the spatial variations across the x-ray beam, and due to differences in the size of the patient's body. Furthermore, structures inside the patients' limbs, in particular bones, arteries and veins, are imaged with a parallax which varies among the sub-images. Consequently, the assembled image formed by the known assembly method contains disturbing transitions at the boundaries of the processed sub-images, as well as substantial pin-cushion distortions which vary over the entire assembled image. These image distortions have a deleterious effect on the diagnostic quality of the assembled image made by the conventional assembly method.

SUMMARY OF THE INVENTION

It is, inter alia, an object of the invention to provide an image composition method such that the influence on the assembled image with artifacts caused by assembly of sub-images is substantially counteracted. It is also an object of the invention to provide an image processor for performing the image composition method in accordance with the invention. It is a further object of the invention to provide an x-ray examination apparatus which is suitable for performing the image composition method according to the invention.

To achieve the object of providing such an image composition method, an image composition method according to the invention is characterized in that merging the sub-images includes a step of interpolation of pixel-values of pixels of mutually overlapping portions of consecutive sub-images which relate to a same position in the elongate scene so as to form pixel-values of the assembled image therefrom.

To achieve the object of providing an image processor for performing the image composition method in accordance with the invention, an image processor in accordance with the invention comprises an interpolation device for interpolating pixel-values of mutually overlapping portions of consecutive sub-images so as to form pixel-values of the assembled image therefrom.

To achieve the object of providing an x-ray examination apparatus which is suitable for performing the method of image assembly according to the invention, an x-ray examination apparatus in accordance with the invention includes an image processor which comprises an interpolation device for interpolating pixel-values of overlapping portions of consecutive sub-images so as to form pixel-values of the assembled image therefrom.

An elongate scene may, for example, consist of an x-ray shadow image of a patient's limb or of a magnetic resonance image of a patient's spine. The elongate scene is imaged by a series of consecutive sub-images. According to the image composition method of this invention, mutually corresponding pixel-values, each pertaining to the same position in the elongate scene, are selected from overlapping portions of consecutive sub-images and are interpolated to form a pixel-value for the position in the elongate scene. It is achieved in this way that sudden transitions in the assembled image at boundaries of regions pertaining to adjacent sub-images are substantially avoided. A pixel-value of a pixel of the assembled image which corresponds to a portion of the elongate scene imaged in overlapping portions of sub-images, is formed from pixel-values of corresponding pixels of the relevant consecutive sub-images, in that a value between the respective pixel-values from the sub-images is supplied through interpolation by a predetermined interpolation function. This interpolation function may e.g. have the form of a weighted sum of the pixel-values from the sub-images.

Especially when the series of sub-images consists of sub-images made by x-irradiation for examination of a patient, the avoidance of such sudden transitions substantially improves the assembled image for use in medical examinations because the assembled image does not contain artifacts formed by said transitions which may obscure lesions, or may inadvertently show an image similar to a lesion whereas the imaged portion of the patient does not comprise any lesions whatsoever. Furthermore, the sub-images may alternatively be formed from a magnetic resonance imaging examination, or from an ultrasound imaging examination. Such imaging modalities may image an elongate scene by forming a consecutive series of sub-images which overlap the elongate scene. It is advantageous for x-ray examinations, as well as for magnetic resonance imaging and ultrasound imaging for diagnostic purposes, to form an assembled image from a series of consecutive sub-images which contain redundant image information.

A preferred implementation of an image composition method according to the invention is characterized in that the merging is preceded by a calculation of the shift with respect to the elongate scene between consecutive sub-images, through a comparison of pixel-values of corresponding pixels of overlapping portions of said consecutive sub-images.

In order to match accurately consecutive sub-images when they are merged into the assembled image, the shift with respect to the elongate scene between consecutive sub-images is determined. When said shift has been determined, the consecutive sub-images can be merged into the assembled image in such a way that the assembled image represents the scene in a continuous way, such that there are no portions deleted between consecutive images, and there are no duplicate portions in the assembled image. In the implementation of the method in accordance with the invention, said relative shift is determined from the image information contained in the sub-images themselves, so that it is not required to perform any measurement relating to the position of the image acquisition means relative to the elongate scene when the sub-images are being formed. In particular said shift is computed from a comparison of pixel-values of pixels in overlapping portions of respective consecutive sub-images which correspond to the same position in the elongate scene.

To perform an implementation of the image composition method according to the invention, an image processor preferably comprises a shift-calculation device for the calculation of the shift with respect to the elongate scene of consecutive sub-images, through the comparison of pixel-values of overlapping portions of said consecutive sub-images.

A further preferred implementation of an image composition method in accordance with the invention is characterized in that a correlation between pixel-values of overlapping portions of said consecutive sub-images is determined as a function of a shift-value between consecutive sub-images, and in that the maximum value of said correlation is formed in order to determine said shift.

In order to accurately calculate said shift between consecutive sub-images, there are determined correlations of pixel-values of pixels in overlapping portions of respective consecutive sub-images and corresponding to the same position in the elongate scene. Such correlations preferably take the form of an average-value of the product of pixel-values of pixels from consecutive sub-images. The correlations are in particular calculated as a function of shift-values of the relative shift between consecutive sub-images. The actual value of said relative shift is subsequently obtained as the shift-value corresponding to the maximum value of the correlations between consecutive sub-images.

An image processor suitable for performing an implementation of the image composition method according to the invention preferably comprises a correlator for determining correlations between pixel-values of overlapping portions of said consecutive sub-images, as a function of a shift-value between consecutive sub-images, and for forming the maximum value of said correlation of each pair of consecutive sub-images.

A further preferred implementation of an image composition method according to the invention is characterized in that a contrasting object is added to the elongate scene which object intentionally induces correlations in overlapping portions of said consecutive sub-images.

When sub-images which are to be merged contain little contrast, the determination of correlations between pixel-values on overlapping portions of consecutive sub-images is improved by the intentional addition of contrast in the sub-images. The contrast in the sub-images is enhanced in accordance with the invention by imaging a contrasting object together with the elongate scene when the elongate scene itself comprises comparatively little contrast. Especially when making sub-images in peripheral angiography, the elongate scene may comprise too little contrast to render an accurate determination of said correlations from the representation of the elongate scene in the sub-images only. Imaging a contrasting object together with the actual elongate scene adds a sufficient amount of contrast to each of the sub-images, to enable the accurate calculation of the relative shift from the correlations.

A further preferred implementation of an image composition method according to the invention is characterized in that the contrasting object has the form of a ruler comprising a binary pattern.

A binary pattern comprises two distinct contrast inducing features. The use of a binary pattern allows the contrasting object, on the one hand, to induce a sufficient amount of contrast in the sub-images, for enabling accurate determination of said correlations, while on the other hand, any obscuration of the elongate scene in the assembled image is substantially limited. It has been found that the contrasting object preferably has the form of a ruler comprising a binary pattern; i.e. the contrasting object comprises a grid pattern of two predetermined distinct features. The use of two features adds contrast to the elongate scene, while the spurious correlations which may be induced are avoided. The presence of only two features assures that the elongate scene, as such, is obscured to a minimal extent; and, since the two features are predetermined, there is minimal interference with features in the elongate scene when one examines an assembled image representing both the elongate scene as such and the contrasting object.

An x-ray examination apparatus which is suitable for performing the image composition method according to the invention, preferably, incorporates a patient support which incorporates a ruler comprising a binary pattern of x-ray absorbing portions and x-ray transmitting portions.

A further preferred implementation of an image composition method according to the invention is characterized in that the ruler has a planar shape and comprises an elongate central feature and first protrusions extending from the central feature in a first direction, and second protrusions extending from the central feature in a second direction, while the pitch between adjacent first protrusions is substantially equal to the pitch between adjacent second protrusions, and the spacing between adjacent first protrusions are offset with respect to the spacing between adjacent second protrusions.

The shape of the ruler is such that the distance between consecutive first protrusions, and between consecutive second protrusions, is comparatively large, but because of an offset between the succession of first protrusions and the succession of second protrusions, the distance between two protrusions of different type is smaller than the distance between consecutive protrusions of the same type. The ruler may be comparatively small, subject to the choice of a size of the sub-images, or of portions of the sub-images, used for the calculation of the shift between consecutive sub-images; nevertheless, there will always be one protrusion of either the first type or the second type which is imaged in each of said possible partial sub-images, but it may be excluded that there are two protrusions of the same kind imaged in each of said partial sub-images. Consequently, the ruler substantially suppresses the introduction of spurious correlations by the ruler. The protrusions may have the shape of bars extending from the central feature; or alternatively, patterns may be employed having a shape being distinct from features in the elongate scene.

An x-ray examination apparatus comprising an image processor for performing an implementation of the image composition method according to the invention preferably comprises a patient support which incorporates a ruler which has a planar shape and comprises an elongate central feature and first protrusions extending from the central feature in a first direction, and second protrusions extending from the central feature in a second direction, and the pitch between adjacent first protrusions being substantially equal to the pitch between adjacent second protrusions, and the spacing between adjacent first protrusions being offset with respect to the spacing between adjacent second protrusions.

A further preferred implementation of an image composition method according to the invention is characterized in that said method includes the selection of respective overlapping lengthened portions of each of the sub-images having respective longitudinal axes substantially transverse to the longitudinal axis of the elongate scene and that said lengthened portions replace the sub-images, and said merging is performed with the lengthened portions so as to form an assembled image.

When consecutive sub-images are made by any imaging means, image distortions often are most abundant away from the centre of each of the sub-images. Such image distortions occur especially when sub-images are made by x-irradiation and x-ray sub-images into visible sub-images are converted by means of an x-ray image intensifier. Notably, each consecutive sub-image shows pin-cushion distortions away from the centre of the sub-image. When an elongate scene is imaged by x-irradiation with the x-ray source and detector being moved along the elongate scene, e.g. along a patient's limb, features in the elongate scene, in this case in the patient's limb, are imaged with a parallax which varies along the direction of motion of the x-ray source. According to the invention, portions of the sub-images are each selected near the centre of a relevant sub-image and said selected portions are employed for the merging into an assembled image whereby pin-cushion distortions are substantially avoided in the assembled image. Moreover, image distortions caused by parallax differences between sub-images are substantially reduced because only portions of the sub-images which have parallax-differences in one direction, viz. perpendicular to the longitudinal axis of the elongate scene, are employed in merging. Any remaining perturbations caused by parallax are minimised in the assembled image because, in the selected portions of the sub-images, the parallax is smaller than in portions of the sub-images outside the selected portions. In order to obtain a sufficient amount of overlap of respective selected lengthened portions, the width of the lengthened portions is preferably chosen to be substantially twice the value of the shift between the consecutive sub-images from which the lengthened portions have been selected.

To implement the image composition method in accordance with the invention, an image processor preferably comprises a field-selector for selecting fields in the form of respective overlapping lengthened portions of each of the sub-images having respective longitudinal axes substantially perpendicular to the longitudinal axis of the elongate scene, which lengthened portions replace the sub-images, and said merging is performed with the lengthened portions so as to form an assembled image.

It is also an object of the invention to provide an image composition method such that the influence on an assembled subtraction image of artifacts caused by assembly of sub-images is substantially counteracted, and an assembled subtraction image being representative of a change in the elongate scene is generated.

To achieve the object of providing such an image composition method, an image composition method according to the invention comprises making a series of consecutive first sub-images, each of them representing a portion of an elongate scene, which first sub-images overlap along the elongate scene. Following a change in the elongate scene, a series of consecutive second sub-images is made, each of them representing a portion of the changed elongate scene, which second sub-images overlap along the changed elongate scene. A series of consecutive subtracted sub-images, which overlap along the (changed) elongate scene, is derived from the respective consecutive series of first and second sub-images. The subtracted sub-images are merged into an assembled subtraction image which is representative of the change in the elongate scene.

A further preferred implementation of an image composition method according to the invention is characterized in that the merging is preceded by a calculation of the shift with respect to the elongate scene of consecutive first sub-images through a comparison of pixel-values of corresponding pixels of overlapping portions of said consecutive first sub-images, and in that the merging is also preceded by a calculation of the relative shift with respect to the (changed) elongate scene of the corresponding first and second sub-images pertaining to substantially corresponding portions of the elongate scene and the changed elongate scene, respectively.

A further preferred implementation of an image composition method according to the invention is characterized in that the merging is preceded by a calculation of the shift with respect to the changed elongate scene of consecutive second sub-images through a comparison of pixel-values of corresponding pixels of overlapping portions of said consecutive second sub-images, and in that the merging is also preceded by a calculation of the relative shift with respect to the elongate scene of corresponding first and second sub-images pertaining to substantially corresponding portions of the elongate scene and the changed elongate scene, respectively.

A further preferred implementation of an image composition method according to the invention is characterized in that the merging is preceded by a calculation of the shift with respect to the (changed) elongate scene of consecutive subtracted sub-images through a comparison of pixel-values of corresponding pixels of overlapping portions of said consecutive subtracted sub-images, and that the merging is also preceded by a calculation of the relative shift with respect to the (changed) elongate scene of corresponding first and second sub-images pertaining to substantially corresponding portions of the elongate scene and the changed elongate scene, respectively.

Changes in the elongate scene are often of particular interest, next to the elongate scene itself. In order to emphasize the changes in the elongate scene, a series of first sub-images FIG. 7a is made which represent an unchanged scene and a series of second sub-images FIG. 7b is made which represent a changed scene. One of these series comprises a feature of particular interest which is absent from the other series; the latter is employed to form mask sub-images. The mask sub-images are subtracted from the images comprising the interesting feature so as to form subtracted sub-images FIG. 7c which are subsequently merged into to an assembled subtraction image containing substantially only the interesting feature. Such situations arise in particular in subtraction angiography. An image of a blood-vessel is made by making an x-ray image of a patient's limb, and an x-ray image of the same limb after an x-ray contrast fluid is administered to the blood-vessel in question. The subimage which is made before the contrast fluid is administered, or after the contrast fluid has disappeared from the blood-vessel, is employed as a mask-image. It is subtracted from the image made with contrast fluid filling the blood-vessel. The resulting subtracted sub-images show substantially only the relevant blood vessel.

In order that the influence of artifacts caused by the assembly of sub-images is substantially counteracted, the translatory-shift between consecutive first or second consecutive sub-images is calculated, and, relative shifts between sub-images and corresponding sub-images which constitute the mask-image are calculated. These shift-calculations are preferably performed through determination of correlations between pixel-values of overlapping portions of relative sub-images. When the relative shift is calculated, an appropriate mask-image is subtracted from the corresponding sub-image containing the interesting feature in such a way that the mask-image substantially contains the same image-information except for the interesting feature. Consequently, the subtraction does not introduce disturbing artifacts. The translatory-shift may be obtained from either one of the first, second, or subtracted sub-images. A translatory-shift may also be determined from the series of consecutive subtracted images instead of from the consecutive series of first or second sub-images.

An image processor suitable for performing an implementation of the image composition method according to the invention is preferably arranged to receive a series of consecutive first sub-images overlapping along an elongate scene, and a series of consecutive second sub-images overlapping along a changed elongate scene, while the image processor preferably comprises subtraction-means for deriving a series of consecutive subtracted sub-images from the first and second sub-images. The image processor also preferably comprises assembly means for merging subtracted sub-images into an assembled subtraction image which is representative of the change in the elongate scene.

To perform an implementation of the image composition method according to the invention an image processor preferably comprises a translation-calculation device for calculating a translatory-shift with respect to the elongate scene of consecutive first sub-images, through a comparison of pixel-values of corresponding pixels of overlapping portions of said consecutive first sub-images, and a correspondence-shift calculation device for calculating a relative shift with respect to the elongate scene between corresponding first and second sub-images pertaining to substantially corresponding portions of the elongate scene and of the changed elongate scene, respectively.

To perform an implementation of the image composition method according to the invention, an image processor preferably comprises a translation-calculation device for calculating a translatory-shift with respect to the changed elongate scene of consecutive second sub-images, through a comparison of pixel-values of corresponding pixels of overlapping portions of said consecutive second sub-images, and a correspondence-shift calculation device for calculating a relative shift with respect to the elongate scene of corresponding first and second sub-images pertaining to substantially corresponding portions of the elongate scene and of the changed elongate scene, respectively.

To perform an implementation of the image composition method in accordance with the invention, an image processor preferably comprises a translation-calculation device for calculating a translatory-shift with respect to the (changed) elongate scene of consecutive subtracted sub-images, through a comparison of pixel-values of corresponding pixels of overlapping portions of said consecutive subtracted sub-images, and a correspondence-shift calculation device for calculating a relative shift with respect to the elongate scene of corresponding first and second sub-images pertaining to substantially corresponding portions of the elongate scene and of the changed elongate scene, respectively.

A further preferred implementation of an image composition method in accordance with the invention is characterized in that merging of the sub-images includes in interpolation of pixel-values of pixels of overlapping respective portions of consecutive subtracted sub-images which relate to a same position in the elongate scene so as to form pixel-values of the assembled subtraction image therefrom.

In order to counteract image artifacts and distortions in the assembled subtraction image pixel-values from overlapping portions of consecutive subtracted sub-images, even more, respective pixel-values each pertaining to the same position in the elongate scene are selected, and these respective pixel-values are interpolated so as to form a pixel-value for the position in the (changed) elongate scene in the assembled subtraction image. In this way it is achieved that sudden transitions in the assembled subtraction image at boundaries of regions pertaining to adjacent sub-images are substantially avoided.

An image processor suitable for performing an implementation of the image composition method in accordance with the invention preferably comprises an interpolation device for the interpolation of pixel-values of overlapping portions of consecutive subtracted sub-images so as to form pixel-values of the assembled subtraction image.

An x-ray examination apparatus comprising an x-ray source for emitting an x-ray beam, an x-ray detector facing the x-ray source, the apparatus comprising a patient-support, the x-ray source, the x-ray detector and the patient-support being moveable with respect to one another so as to enable the formation of a series of consecutive images of an elongate portion of the patient and by x-irradiation of successive portions of the patient, and which apparatus is suitable for performing the image composition method in according to the invention preferably comprises an image processor.

A preferred embodiment of an x-ray examination apparatus according to the invention preferably comprises x-ray absorption means which can be arranged between the x-ray source and the x-ray detector in order to attenuate the x-ray beam and to shape the cross-section of the x-ray beam transverse to a central ray of the x-ray beam, and is characterized in that the image processor comprises a field-selector for selecting fields in the form of respective overlapping lengthened portions of each of the sub-images having respective longitudinal axes substantially perpendicular to the longitudinal axis of the elongate scene and that said lengthened portions replace the sub-images and said merging is performed with the lengthened portions to form an assembled image and in that the x-ray absorption means are positionable relative to the x-ray beam-path and controlled by the field-selector for selecting of overlapping lengthened portions.

X-ray absorption means, such as positionable x-ray shutters substantially block out portions of the x-ray beam so that a controlled portion of a patient is x-irradiated. It is advantageous to employ the x-ray absorption means for selecting the lengthened portions of the sub-images that are actually used in the formation of the assembled (subtraction) image because it enables a reduction in the x-ray dose to which the patient is exposed during a radiological examination.

BRIEF DESCRIPTION OF THE DRAWING

These and other aspects of the invention will become apparent from and will be elucidated with reference to the implementations and embodiments described hereinafter and with reference to the accompanying drawings, in which.

DETAILED DESCRIPTION OF THE PREFERRED EMBODIMENTS

Figure 1:
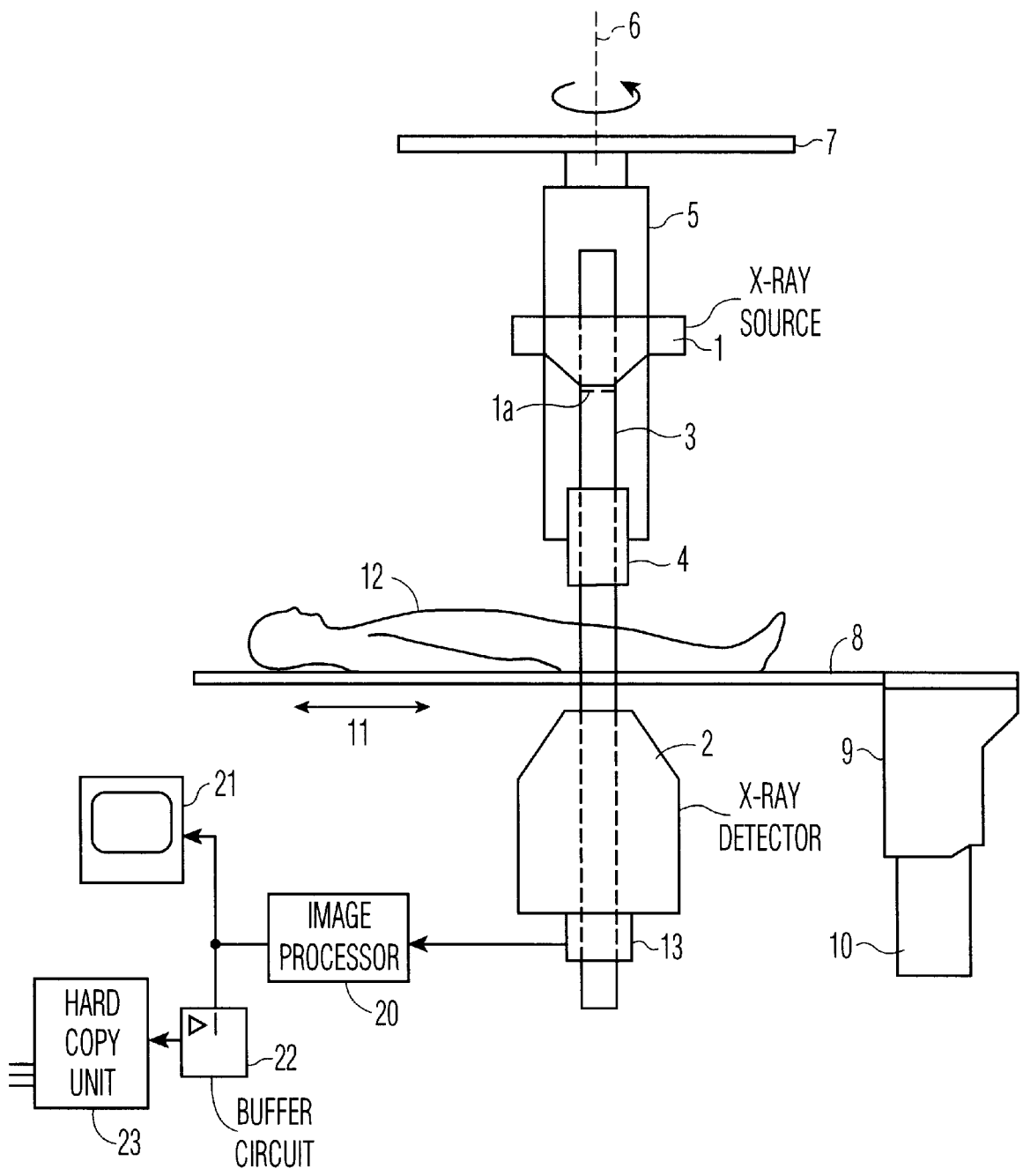
FIG. 1 shows a side elevation of an x-ray examination apparatus in accordance with the invention.

FIG. 1 shows a side elevation of an x-ray examination apparatus in accordance with the invention. An x-ray source 1 with optional x-ray absorbing shutter 1a and an x-ray detector 2, e.g. an x-ray image intensifier, are connected to a carrier 3, e.g. a C-arm. The C-arm is movably mounted to a predominantly vertical support 5 by means of a sleeve 4. The vertical support is rotatable around a predominantly vertical axis 6 of rotation and the vertical support is mounted to a system of guide rails 7 which are attached to the ceiling of the room in which the x-ray apparatus is installed. The patient table 8 is mounted to a table frame 9 which is mounted to a pillar 10. The frame is moveable along the pillar, so as to adjust the height of the patient table above the x-ray source. The table 8 is also movably connected to the frame so as to allow longitudinal 11 displacement of the patient table with the patient 12. The x-ray image intensifier 2 converts an x-ray image formed on the entrance screen of the image intensifier into a light-image on the output window of the image intensifier. The light-image is registered by a system of lenses and a videocamera 13. The videocamera 13 provides an electronic video signal for each of the registered images, which videosignals are supplied to an image processor 20 which merges electronic sub-images into an assembled image in the form of an electronic image signal which may be supplied to a monitor 21 for viewing or to a buffer circuit 22 for further processing, e.g. for supplying the electronic image signal to a hard-copy unit 23 for making a hard-copy of the assembled image.

For performing peripheral angiography, e.g. x-ray imaging of a bloodflow in a patient's leg, a contrast fluid is administered intra-arterially and the progress of the contrast fluid is monitored in that the patient table or the carrier is moved along with the contrast fluid. During the motion of the carrier and/or the patient, a plurality of x-ray exposures is performed. The videocamera 13 supplies videosignals for consecutive sub-images corresponding to consecutive x-ray images which are formed on the entrance screen of the image intensifier. The consecutive sub-images are merged into an assembled image by the image processor 20. The blood-flow through the entire leg of the patient can then be examined from one single assembled image that shows a shadow image of the complete leg.

Figure 2:
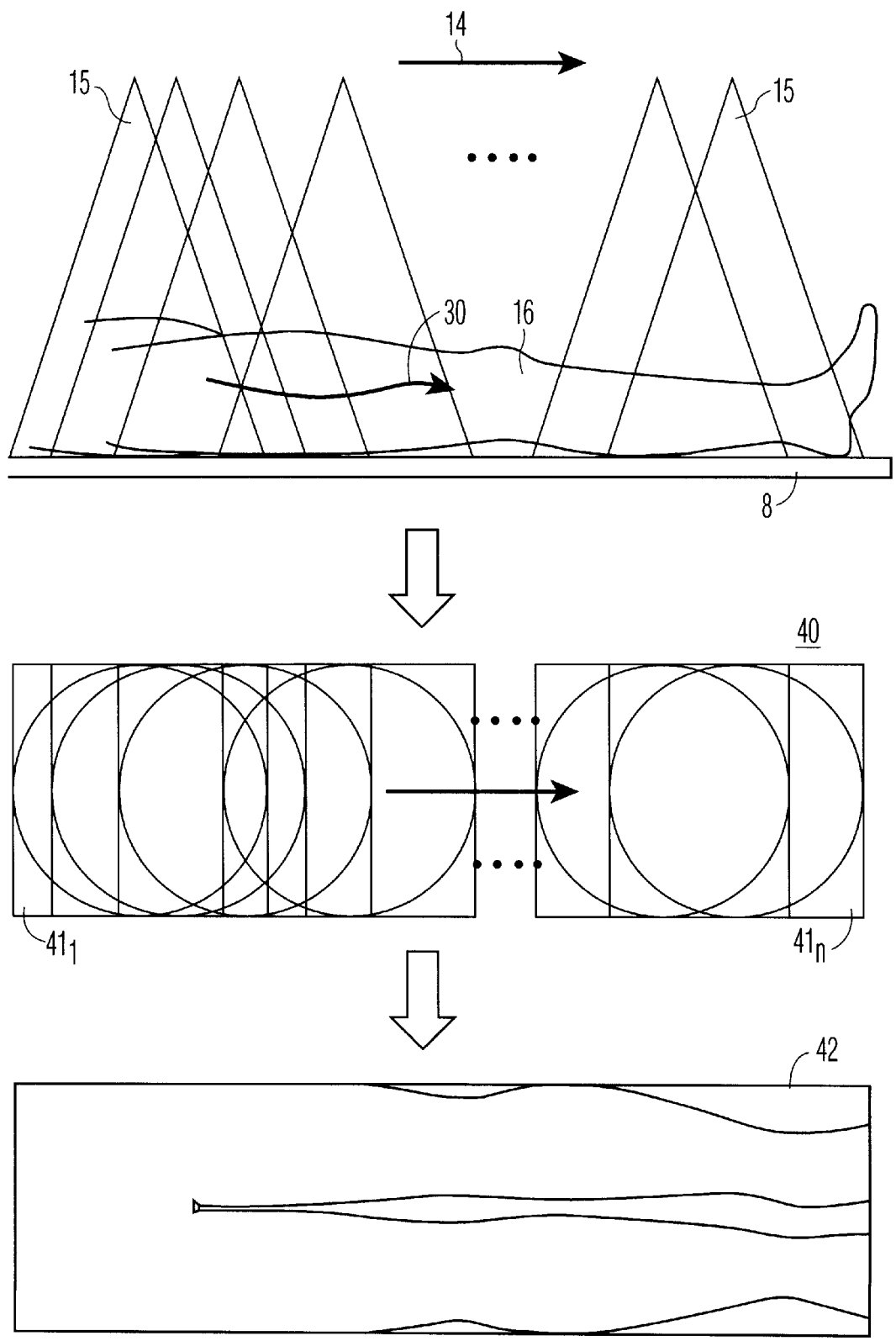
FIG. 2 shows a diagrammatic representation of the formation of sub-images and the assembly of an assembled image from the consecutive sub-images.

FIG. 2 shows a diagrammatic representation of the formation of sub-images and the merging of consecutive sub-images into an assembled image. A patient's leg 16 is shown on the patient table 8. The vertical support 5 is moved along the rails 7, so that the x-ray source is moved in the direction of the arrow 14. As the x-ray source is moved, an x-ray beam 15 is intermittently directed at the patient's leg. The motion of the x-ray source is controlled with respect to the progress of contrast fluid in a blood vessel in the patient's leg as indicated by the arrow 30. Together with the x-ray source the image intensifier is also moved so as to face the x-ray source when the patient is irradiated. This is achieved in that the x-ray source and the image intensifier are mounted to the carrier which is attached to the vertical stand. Whenever the patient's leg is irradiated an x-ray sub-image is formed on the entrance screen of the image intensifier. Thus, a collection 40 is formed of consecutive images $41_1$ to $41_n$ which mutually overlap to various degrees. The overlap between sub-images depends on the displacement between positions of the x-ray source at the irradiation for forming said sub-images. The image processor 20 merges the sub-images of the collection 40 into an assembled image 42 which contains a shadow-image of the entire patient's leg.

Figure 3:
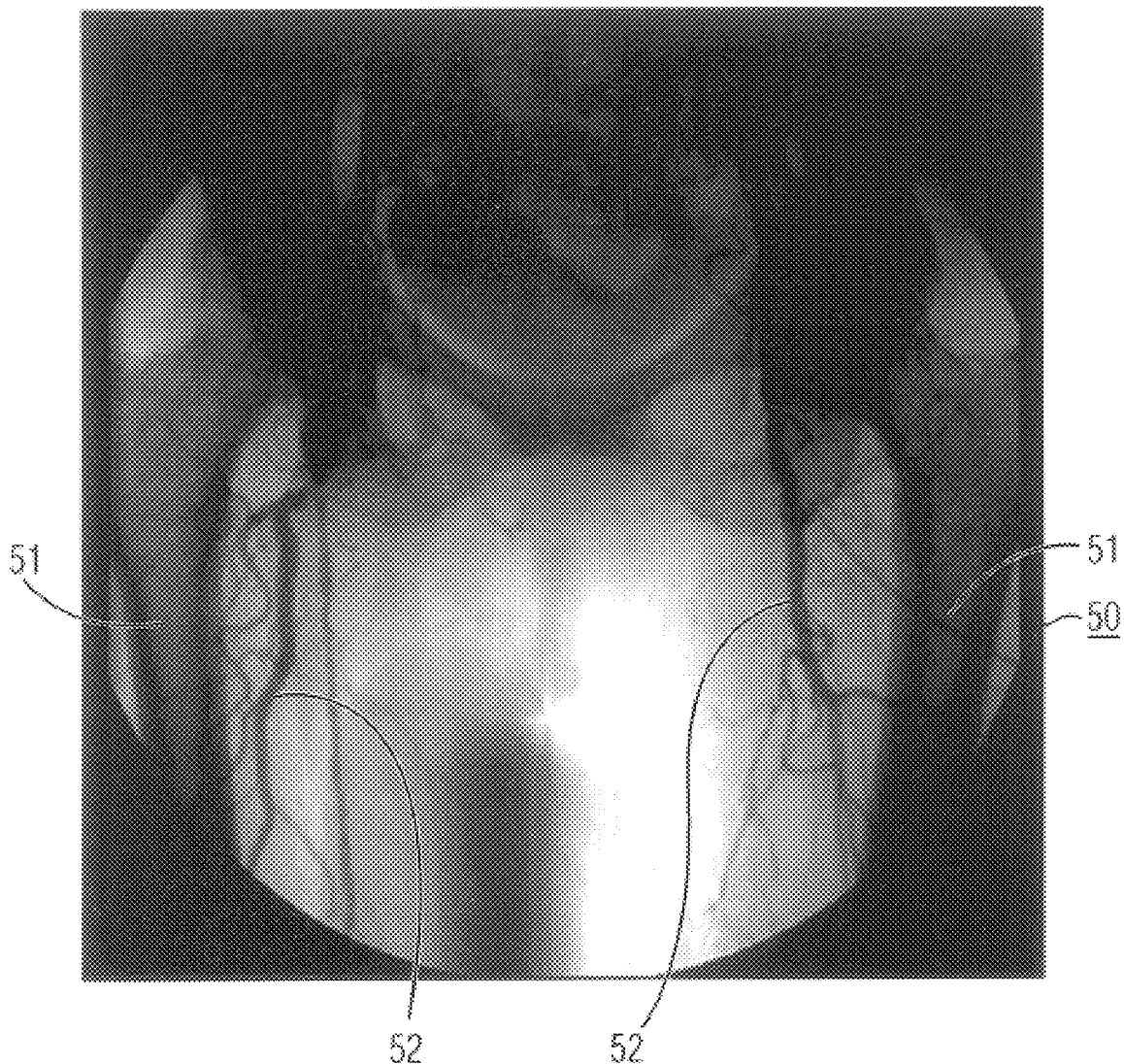
FIG. 3 shows an example of a sub-image which is involved in the assembly of an assembled image.

FIG. 3 shows an example of a sub-image which is involved in the assembly of an assembled image. A representation 50 of an image registered by the videocamera 13 shows a shadow image of a section at the groin-area of the patient's legs. The image is circular owing to the circular shape of the exit window of the image intensifier. The shadow image features the thigh bones 51 and arteries 52 which are filled with contrast fluid.

Figure 4:
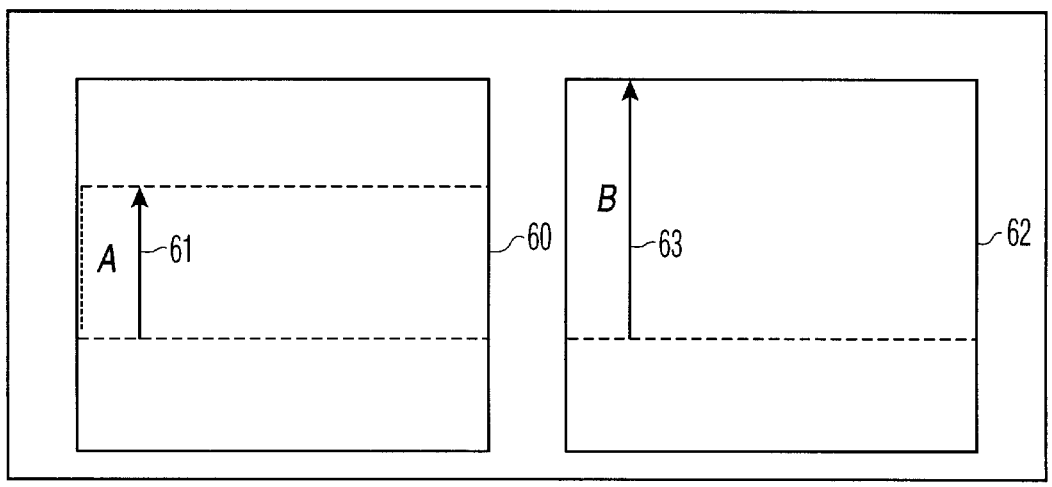
FIG. 4 illustrates the choice of a gauge vector from a first sub-image and of a template vector from a second sub-image.

FIG. 4 illustrates the choice of a template vector from a first sub-image and of a gauge vector from a second sub-image. A patient's limb, e.g. a leg, is assumed to be imaged such that the longitudinal axis of the limb is along the column-direction of the pixel-matrices of the consecutive sub-images. A template vector A 61 of e.g. 64 pixels in a column of the pixel-matrix 60 is selected in the pixel-matrix 60 of the N-th sub-image. In the pixel-matrix 62 of the (N+1)-st sub-image a gauge vector B, of e.g. 192 pixels is selected in a column of the pixel-matrix of the (N+1)-st sub-image. The correlation of the template vector with the gauge vector is computed as a function of shift the (N+1)-st sub-image with respect to the N-the sub-image. The correlation-value of those two vectors is defined as $$C_p = [\Sigma_k A_k B_k] / \{[\Sigma_k |A_k|^p]^{1/p} [\Sigma_k |B_k|^{p/(p-1)}]^{(p-1)/p}\}$$

The correlation-value with p=2 is found to be a particularly advantageous quantity for determining the mutual shift between successive sub-images. Because of the Cauchy-Schwarz inequality, which is by the way a special case of the Hölder inequality when p=2, the correlation-value has the value 1 as its maximum value and attains its maximum value when the template vector perfectly matches with the gauge vector; that is, when the template vector is positioned with respect to the gauge vector so that ail pixel-elements of the template vector have the same value as corresponding pixel-elements of the gauge vector. Because of small distortions and noise it may occur that the correlation-value does not reach the value 1. The shift of the (N+1)-st sub-image with respect to the N-th sub-image is defined as the shift-value for which the correlation-value as a function of the shift-value attains its maximum value. Special portions of the sub-images are seleted for determining the template vector and the gauge vector The calculation of the shift on the basis of the correlation-value of the template vector and gauge vector in portions of the image where there is hardly any contrast which would provide an erroneous result in that there may seem to be no shift at all. Those columns of the pixel-matrices of the sub-images wherein shadow-images of the legs appear are preferably employed for computing mutual shift between consecutive sub-images in the case of peripheral angiography of a patient's legs. In particular with sub-images of 512 columns it is found that virtually any patient's legs are in the columns #40 to #160 and in the columns #352 to #472. These ranges appear adequate for containing shadow images of virtually any adult patient's legs, no matter the precise dimensions of the patient who is to be examined. The columns in the ranges of the columns #40 to #160 and the columns in the range #352 to #472 are selected as the special portions of the sub-images from which the gauge and template vectors are selected. A further refinement may be achieved by noting that the ranges of columns taper towards the patient's feet, and selecting the columns for comparison more in accordance with the patient's anatomy.

Figure 5:
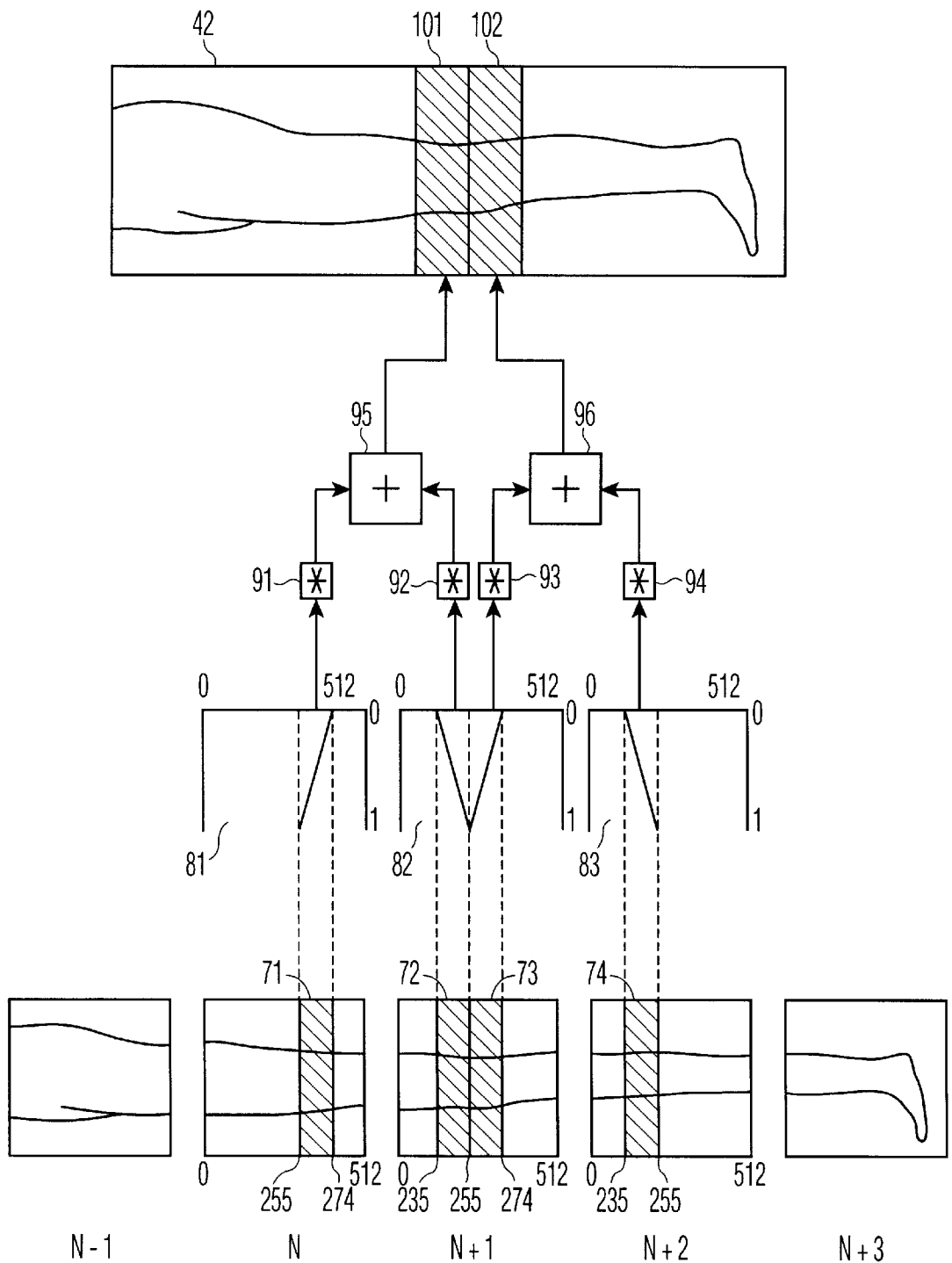
FIG. 5 illustrates the merging of sub-images into an assembled image in accordance with the invention.

FIG. 5 illustrates the merging of sub-images into an assembled image in accordance with the invention. Three consecutive sub-images numbered N, N+1 and N+2 are shown. The scenes in the consecutive images have mutual overlap. The shift between the scenes in one sub-image with respect to the same scene in the next sub-image is computed as discussed hereinbefore in relation to FIG. 4. The pixel-matrices of consecutive sub-images are arranged such that the shift is perpendicular to the rows of the respective matrices, i.e. the mutual shift is expressed as a number of rows. In each pair of consecutive sub-images, respective sections are selected by the field selection 70 comprising the same portion of the scene. In each of the sub-images the selected section is located near a central row of that sub-image. Specifically in FIG. 5, in the sub-image N the selected section 71 comprises the rows #255 to #274. In the next sub-image, i.e. the sub-image N+1, the rows #235 to #254 are selected as the selected section 72. This example pertains to a pair of consecutive sub-images comprising a mutual shift of 20 rows. Subsequently, the pixels in the selected section 71 in sub-image N are multiplied by a first weight-factor which has a value which decreases from 1 for the first row (#255) of the section 71 to 0 for the final row (#274) of the section 71. The pixels in the selected section 72 in sub-image N+1 are multiplied by a second weight-factor that has a value which increases from 0 for the first row (#235) of the section 71 to 1 for the final row (#254) of the section 71. The first and second weight factors are such that the sum of the first weight factor for a row in section 71 and the second weight factor for a row in section 72 with the same relative position within section 72 as the relative position of said row in section 71 is substantially constant and equals the value 1. Weight factors that vary linearly as a function of the rows in a section are preferred for this. The variation of relevant weight-factors as a function of row-numbers of relevant sections are depicted in the graphs 81, 82, and 83. The multiplication of pixel-values by relevant weight-factors is indicated schematically by the multipliers 91, 92, 93 and 94 provides weighted pixel-values of rows of sections 71 and 72. Weighted pixel-values of sections 71 are added to weighted pixel-values pertaining to sections 72 such that weighted pixel-values of pixels pertaining to the same position in the scene are added by an addition device 95 each time. The addition of weighted pixels of rows of respective sections produces rows of pixel-values for the assembled image 42. A section 101 of the assembled image is formed from the sections 71 and 72. A section 73 of the sub-image N+1 and a section 74 of the sub-image N+2 are selected in a similar manner, the sub-images 73 and 74 pertaining to the same portion of the scene and said same portion of the scene being slightly shifted with respect to the portion of the scene which is represented in the two sections 71 and 72. Pixel-values of corresponding rows of sections 73 and 74 are multiplied by weight-factors so as to form weighted pixel-values similar to the formation of weighted pixel-values from sections 71 and 72 as discussed hereinbefore. A subsequent section 102 of the assembled image is formed from weighted pixel-values formed from the sections 73 and 74 through addition of an addition device 96 these weighted pixel-values of the sections 73 and 74 and of pixels pertaining to the same position in the scene. The sections 101 and 102 of the assembled image comprise image information on adjacent portions of the scene which is imaged by the camera 13 and which are represented by the sub-images. The sub-images are to be merged into an assembled image representing the entire scene in a single image. Therefore, the section 102 is positioned in the assembled image next to the section 101. To form the entire image, the formation of sections of the assembled image from sections of sub-images which overlap in the scene is re-iterated. Finally, at the extremities of the assembled image, portions of the first and last sub-images of the consecutive series are added. The assembled image then embraces the extremities of the elongate scene, notably the groin-area of the patient and the patient's feet. It is relevant in peripheral angiography of a patient's leg that these extremities are imaged in the assembled image, so that the entire flow of contrast fluid is contained in the assembled image and anatomical orientation in the assembled image is facilitated.

Only image information from sections of sub-images is used in the assembled image, such that in each of the respective sub-images only sections near respective central axes of the relevant sub-images are selected. The rows of the pixel-matrices of the sub-images are arranged perpendicularly to the direction of the mutual shift between the consecutive-sub-images, so that there is almost no parallax error between corresponding rows of consecutive sub-images. Furthermore, the pin-cushion distortion caused by the curvature of the entrance screen of the image intensifier 2 is smaller in portions near the centre of each of the sub-images.

Figure 6A:
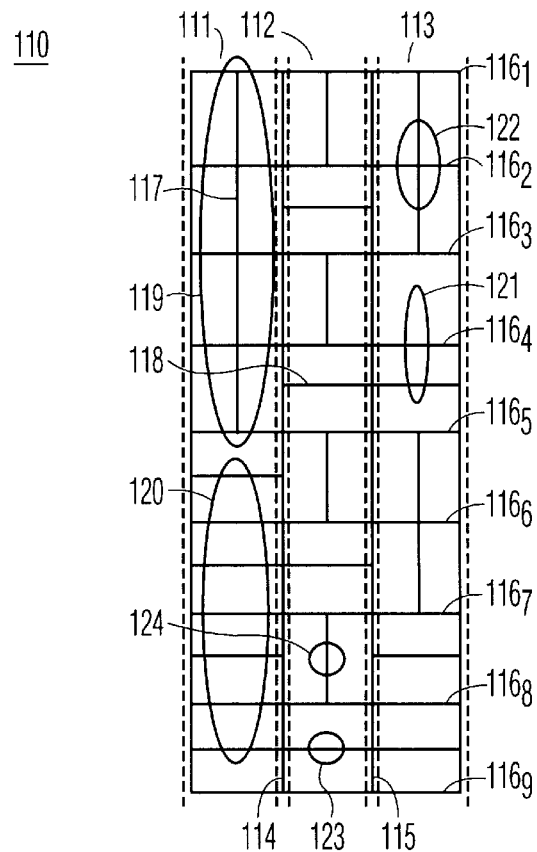
FIGS. 6a and 6b illustrate respective embodiments of contrasting objects having the form of a planar ruler having a binary pattern.
Figure 6B:
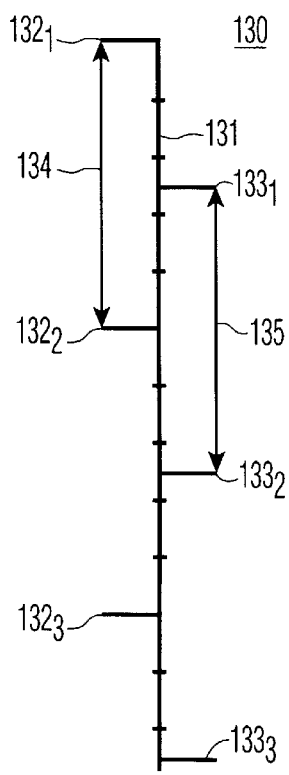

FIGS. 6a and 6b illustrate respective embodiments of contrasting objects having the shape of a planar ruler with a binary pattern. The ruler of FIG. 6a is formed from a steel grid which partly absorbs x-radiation. The ruler is placed between the patient and the x-ray detector during x-irradiation and consequently a shadow image of the ruler is formed within the shadow image of the patient. The ruler 110 of FIG. 6a comprises a pattern of a plurality of columns, three of which 111, 112 and 113 are shown. Adjacent columns share a longitudinal bar, explicitly, columns 111 and 112 share the longitudinal bar 114 and the columns 112 and 113 share the longitudinal bar 115. The ruler 110 further comprises transverse bars $116_{1-9}$ extending across the width of the ruler. In between adjacent transverse bars there is placed either a bar-section in the longitudinal direction, such as the longitudinal bar-section 117 between the adjacent transverse bars $116_2$ and $116_3$, or a bar-section in the transverse direction, such as the transverse bar-section 118 between the transverse bars $116_4$ and $116_5$, which connects the longitudinal bars 114 and 115. In each of the columns the longitudinal bar sections are arranged in groups which alternate with groups of transverse bar-sections. Column 111 shows one group 119 of longitudinal bar-sections and one group 120 of transverse bar-sections. In column 113 the groups of transverse and longitudinal bar-sections, e.g. 121 and 122 respectively, are alternating with a frequency which is twice the frequency of the alternation in column 111. In column 112 the groups of transverse and longitudinal bar-sections, e.g. 123 and 124, respectively, alternate with a frequency which is twice the frequency of the alternation in column 112. That contrast is thus created in the shadow image with various spatial frequencies so that correlations in consecutive sub-images formed with the use of the ruler 110 are induced at various spatial frequencies. The pattern of the ruler 110 is of binary nature viz. a longitudinal bar-section is interpreted as a 1 and transverse bar-sections is interpreted as a 0, or vice versa.

FIG. 6b shows another embodiment of a contrasting object in the form of a planar ruler 130. The ruler 130 comprises an elongate central feature, in particular a longitudinal bar 131. From the longitudinal bar 131 first protrusions $132_{1-3}$ extend in a transverse direction. Second protrusions $133_{1-3}$ also extend from the longitudinal bar, in such a way that the longitudinal bar and the first and second protrusions are in the plane of the ruler. In the embodiment depicted here the first and second protrusions extend perpendicularly from the longitudinal bar. However, other embodiments may be constructed where the first and second protrusions enclose oblique angles with the longitudinal bar. The spacing between adjacent first protrusions such as the spacing 134 between the first protrusions $132_1$ and $132_2$ are shifted with respect to adjacent second protrusions such as the spacing 135 between the second protrusions $133_1$ and $133_2$. The binary nature of the ruler 130 is understood by interpreting a first protrusion as a 1 and a second protrusion as a 0, or vice versa. Because of the shift between spacings between adjacent protrusions of respective types, the choice of the template vector employed for computing the correlation of adjacent sub-images can be made in such a way that there is always one single protrusion of the same type, i.e. either a single first protrusion and/or a single second protrusion, comprised in the template vector. Consequently, the ruler induces correlations between consecutive sub-images but no spurious correlations pertaining to values of the shift substantially different from the actual shift between consecutive sub-images are induced. When a ruler is employed which has protrusions enclosing oblique angles with the central feature, then spurious correlations are avoided in situations where the series of consecutive sub-image is made while (unintentionally) translating the x-ray detector at an angle with the axis of the elongate scene. A further particular advantage of the ruler 130 is that it adds comparatively small features to the sub-images and the image of the ruler consequently does not substantially deteriorate the diagnostic quality of the assembled image.

The fact that the pattern of both rulers 110 and 130 are predetermined and have a binary nature renders it comparatively simple to delete the image of the ruler from the assembled image by digital electronic post-processing of the assembled image.

Contrasting objects, such as the ruler 110 and the ruler 130 may preferably be incorporated in the patient table.

It is noted that the functions of the image processor may be performed by a suitably programmed computer or by a special purpose processor having circuit means that are arranged to perform said functions in an image processor in accordance with the invention.

We claim:

1. An medical image composition method for composing an assembled image, said assembled image comprising pixels corresponding to positions in an elongate scene, said method comprising the steps of:

making a series of consecutive sub-images, wherein each sub-image represents a portion of the elongate scene, pairs of consecutive sub-images overlap along the elongate scene, and each pixel of the assembled image is in the overlapping portion of at least one pair of consecutive sub-images, and merging the sub-images into said assembled image by forming a pixel-value for each pixel in the assembled image by the steps of:

selecting a pair of consecutive sub-images in whose overlapping portion is said pixel of the assembled image, selecting pixels in each sub-image of said selected pair of consecutive sub-images which relate to the same position in the elongate scene as said pixel of the assembled image, and assigning a pixel-value to said pixel in said assembled image based upon an interpolation of the pixel-values of each of said selected pixels in each sub-image of said selected pair of consecutive sub-images.

2. An image composition method as claimed in claim 1, characterized in that the merging is preceded by a calculation of the shift with respect to the elongate scene between pairs of consecutive sub-images through comparison of pixel-values of corresponding pixels of overlapping portions of said pairs of consecutive sub-images.

3. An image composition method as claimed in claim 2, characterized in that a correlation between pixel-values of overlapping portions of said pairs of consecutive sub-images is determined as a function of a shift-value between said pairs of consecutive sub-images and the maximum value of said correlation is formed in order to determine said shift.

4. An image composition method as claimed in claim 3, characterized in that a planar contrasting object is added to the elongate scene which object intentionally induces correlations in overlapping portions of said pairs of consecutive sub-images.

5. An image composition method as claimed in claim 4, characterized in that the planar contrasting object has the form of a ruler comprising a binary pattern.

6. An image composition method as claimed in claim 5, characterized in that the ruler has a planar shape and comprises an elongate central feature and first protrusions extending from the central feature in a first direction, and second protrusions extending from the central feature in a second direction and the pitch between adjacent first protrusions being substantially equal to the pitch between adjacent second protrusions and the spacing between adjacent first protrusions are offset with respect to the spacing between adjacent second protrusions.

7. An image composition method as claimed in claim 1, characterized in that said method includes the selection of respective overlapping consecutive lengthened portions of each of the overlapping consecutive sub-images having respective longitudinal axes substantially transverse to the longitudinal axis of the elongate scene and that said overlapping consecutive lengthened portions replace the overlapping consecutive sub-images and said merging is performed with the overlapping consecutive lengthened portions so as to form an assembled image.

8. The method of claim 1 wherein said interpolation of the pixel-values is a weighted linear interpolation in which said weights vary monotonically along a direction of shift between overlapping pairs of consecutive sub-images along the elongate scene.

9. The method of claim 8 wherein said monotonic variation of said weights associated with each overlapping consecutive sub-image is a monotonic decrease from a more central region to a more peripheral region of each overlapping consecutive sub-image.

10. An medical image composition method for composing an assembled subtraction image, said assembled subtraction image comprising pixels corresponding to positions in an elongate scene, said method comprising the steps of
making a series of consecutive first sub-images, wherein each first sub-image, wherein said sub-images are differently shifted with respect to the elongate scene and represents a portion of the elongate scene and pairs of consecutive first sub-images overlap along the elongate scene,
making a series of consecutive second sub-images, wherein said sub-images are differently shifted with respect to the elongate scene and following a change in the elongate scene, wherein each second sub-image represents a portion of the changed elongate scene and pairs of second sub-images overlap along the changed elongate scene,
making a series of consecutive subtracted sub-images from the respective series of consecutive first and second sub-images, wherein pairs of consecutive subtracted sub-images overlap along the elongate scene, and each pixel of the assembled subtraction image is in the overlapping portion of at least one pair of consecutive subtracted sub-images, and
merging the series of consecutive subtracted sub-images into the assembled subtraction image by forming a pixel-value for each pixel in the assembled subtraction image by the steps of:
selecting a pair of consecutive subtracted sub-images in whose overlapping portion is said pixel of the assembled subtraction image,
selecting pixels in each subtracted sub-image of said selected pair of consecutive subtracted sub-images which relate to the same position in the elongate scene as said pixel of the assembled subtraction image, and
assigning a pixel-value to said pixel in said assembled subtraction image based upon an interpolation of the pixel-values of each of said selected pixels in each subtracted sub-image of said selected pair of consecutive subtraction sub-images.

11. An image composition method as claimed in claim 10, characterized in that the merging is preceded by a calculation of the shift with respect to the elongate scene of pairs of overlapping consecutive first sub-images through comparison of pixel-values of corresponding pixels of overlapping portions of said pairs of overlapping consecutive first sub-images and in that the merging is also preceded by a calculation of the relative shift with respect to the (changed) elongate scene of corresponding first and second sub-images pertaining to substantially corresponding portions of the elongate scene and the changed elongate scene, respectively.

12. An image composition method as claimed in claim 10, characterized in that the merging is preceded by calculation of the shift with respect to the changed elongate scene of pairs of overlapping consecutive second sub-images through comparison of pixel-values of corresponding pixels of overlapping portions of said pairs of overlapping consecutive second sub-images and in that the merging is also preceded by calculation of the relative shift with respect to the elongate scene of corresponding first and second sub-images pertaining to substantially corresponding portions of the elongate scene and the changed elongate scene, respectively.

13. An image composition method as claimed in claim 10, characterized in that the merging is preceded by calculation of the shift with respect to the (changed) elongate scene of pairs of overlapping consecutive subtracted sub-images through comparison of pixel-values of corresponding pixels of overlapping portions of said pairs of overlapping consecutive subtracted sub-images and that the merging is also preceded by calculation of the relative shift with respect to the (changed) elongate scene of corresponding first and second sub-images pertaining to substantially corresponding portions of the elongate scene and the changed elongate scene, respectively.

14. The method of claim 10 wherein said interpolation of the pixel-values is a weighted linear interpolation in which said weights vary monotonically along a direction of shift between overlapping pairs of consecutive sub-images along the elongate scene.

15. The method of claim 14 wherein said monotonic variation of said weights associated with each overlapping consecutive sub-image is a monotonic decrease from a more central region to a more peripheral region of each overlapping consecutive sub-image.

16. An medical image processor for composing an assembled image, said assembled image comprising pixels corresponding to positions in an elongate scene by processing a series of consecutive sub-images, wherein each sub-image represents a portion of the elongate scene, pairs of consecutive sub-images wherein said sub-images are differently shifted with respect to the elongate scene and overlap along the elongate scene, and each pixel of the assembled image is in the overlapping portion of at least one pair of consecutive sub-images, the image processor comprising an assembly means for merging the series of consecutive sub-images by forming a pixel-value for each pixel in the assembled image by the steps of:

selecting a pair of consecutive sub-images in whose overlapping portion is said pixel of the assembled image, selecting pixels in each sub-image of said selected pair of consecutive sub-images which relate to the same position in the elongate scene as said pixel of the assembled image, and assigning a pixel-value to said pixel in said assembled image based upon an interpolation of the pixel-values of each of said selected pixels in each sub-image of said selected pair of consecutive sub-images.

17. An image processor as claimed in claim 16 further comprising a correlator for determining correlations of pixel-values of overlapping portions of said pairs of overlapping consecutive sub-images as a function of a shift-value between consecutive sub-images and for forming the maximum value of said correlations of pairs of successive sub-images.

18. An x-ray examination apparatus comprising
an x-ray source for emitting an x-ray beam,
an x-ray detector facing the x-ray source,
a patient-support, wherein the x-ray source, the x-ray detector and the patient-support are moveable with respect to one another so as to enable the formation of a series of consecutive sub-images of an elongate portion of the patient by x-irradiation of successive portions of the patient, and
an image processor as claimed in claim 13 for composing the series of consecutive sub-images into an assembled image of the elongate portion of the patient.

19. An x-ray examination apparatus as claimed in claim 18 characterized in that the patient-support incorporates a planar ruler comprising a binary pattern of x-ray absorbing portions and x-ray transmitting portions.

20. An x-ray examination apparatus as claimed in claim 18, comprising x-ray absorption means which can be arranged between the x-ray source and the x-ray detector in order to attenuate the x-ray beam and to shape the cross-section of the x-ray beam transverse to a central ray of the x-ray beam, wherein the x-ray absorption means are positionable relative to the x-ray beam-path to produce overlapping pairs of consecutive lengthened portions of each of the overlapping pairs of consecutive sub-images having respective longitudinal axes substantially perpendicular to the longitudinal axis of the elongate scene, and wherein the image processor processes the overlapping pairs of consecutive lengthened portions such that said overlapping pairs of consecutive lengthened portions replace the overlapping pairs of consecutive sub-images and said merging is performed with the overlapping pairs of consecutive lengthened portions to form the assembled image.

21. The method of claim 16 wherein said interpolation of the pixel-values is a weighted linear interpolation in which said weights vary monotonically along a direction of shift between overlapping pairs of consecutive sub-images along the elongate scene.

22. The method of claim 21 wherein said monotonic variation of said weights associated with each overlapping consecutive sub-image is a monotonic decrease from a more central region to a more peripheral region of each overlapping consecutive sub-image.

23. An medical image processor for composing an assembled subtraction image, said assembled subtraction image comprising pixels corresponding to positions in an elongate scene, wherein said image processor is (i) arranged to receive a series of consecutive first sub-images, wherein each consecutive first sub-image represents a portion of an elongate scene and pairs of consecutive first sub-images wherein said sub-images are differently shifted with respect to the elongate scene and overlap along the elongate scene, and is (ii) arranged to receive a series of consecutive second sub-images following a change in the elongate scene, wherein each second sub-image represents a portion of the changed elongate scene and pairs of consecutive second sub-images wherein said sub-images are differently shifted with respect to the elongate scene and overlap along the changed elongate scene, and wherein the image processor comprises (i) subtraction means for deriving a series of consecutive subtracted sub-images from the respective series of consecutive first and second sub-images, wherein pairs of consecutive subtracted sub-images overlap along the elongate scene, and each pixel of the assembled subtraction image is in the overlapping portion of at least one pair of consecutive subtracted sub-images, and (ii) assembly means for merging the series of consecutive subtracted sub-images into an assembled subtraction image by forming a pixel-value for each pixel in the assembled subtraction image by the steps of:

selecting a pair of consecutive subtracted sub-images in whose overlapping portion is said pixel of the assembled subtraction image, selecting pixels in each subtracted sub-image of said selected pair of consecutive subtracted sub-images which relate to the same position in the elongate scene as said pixel of the assembled subtraction image, and assigning a pixel-value to said pixel in said assembled subtraction image based upon an interpolation of the pixel-values of each of said selected pixels in each subtracted sub-image of said selected pair of consecutive subtraction sub-images.

24. An x-ray examination apparatus comprising
an x-ray source for emitting an x-ray beam,
an x-ray detector facing the x-ray source,
a patient-support, wherein the x-ray source, the x-ray detector and the patient-support are moveable with respect to one another so as to enable the formation of series of consecutive sub-images of an elongate portion of the patient by x-irradiation of successive portions of the patient, and
an image processor as claimed in claim 23 for composing series of consecutive sub-images into an assembled image of the elongate portion of the patient.

25. The method of claim 23 wherein said interpolation of the pixel-values is a weighted linear interpolation in which said weights vary monotonically along a direction of shift between overlapping pairs of consecutive sub-images along the elongate scene.

26. The method of claim 25 wherein said monotonic variation of said weights associated with each overlapping consecutive sub-image is a monotonic decrease from a more central region to a more peripheral region of each overlapping consecutive sub-image.

* * * * *